United States Patent [19]

Tezuka et al.

[11] 4,089,830

[45] May 16, 1978

[54] SETTING SOLUTION FOR DENTAL GLASS IONOMER CEMENTS

[75] Inventors: Chojiro Tezuka, Tokyo; Yoshimitsu Karasawa, Takasaki, both of Japan

[73] Assignee: G-C Dental Industrial Corp., Tokyo, Japan

[21] Appl. No.: 731,470

[22] Filed: Oct. 8, 1976

[30] Foreign Application Priority Data

Feb. 24, 1976  Japan ................... 51-18480

[51] Int. Cl.$^2$ ................................. C08K 3/40
[52] U.S. Cl. .................. 260/29.6 H; 32/15; 106/35; 260/29.6 S
[58] Field of Search ............ 106/35; 260/29.6 S, 260/29.6 H, 29.6 M; 32/15

[56] References Cited

U.S. PATENT DOCUMENTS

| | | | |
|---|---|---|---|
| 3,655,605 | 4/1972 | Smith et al. | 260/29.6 S |
| 3,741,926 | 6/1973 | Jurecic | 260/29.6 M |
| 3,751,391 | 8/1973 | Smith | 32/15 |
| 3,804,794 | 4/1974 | Schmitt et al. | 32/15 |
| 3,814,717 | 6/1974 | Wilson et al. | 32/15 |
| 3,837,865 | 9/1974 | Pellico | 106/35 |
| 3,856,737 | 12/1974 | Foster et al. | 32/15 |
| 3,882,080 | 5/1975 | Schmitt et al. | 260/29.6 M |
| 3,962,267 | 6/1976 | Suzuki et al. | 32/15 |
| 3,986,998 | 10/1976 | Schmitt et al. | 260/29.6 M |
| 4,016,124 | 4/1977 | Crisp et al. | 260/29.6 M |

FOREIGN PATENT DOCUMENTS

| | | | |
|---|---|---|---|
| 2,301,444 | 7/1973 | Germany | 260/29.6 M |

*Primary Examiner*—Eugene C. Rzucidlo
*Attorney, Agent, or Firm*—Oblon, Fisher, Spivak, McClelland & Maier

[57] ABSTRACT

An aqueous setting solution for dental glass ionomer cements comprising 45 to 60% of polyacrylic acid or acrylic acid copolymer and 7 to 25% of one or more of polybasic carboxylic acids based on the total weight.

3 Claims, No Drawings

SETTING SOLUTION FOR DENTAL GLASS IONOMER CEMENTS

DETAILED DESCRIPTION OF THE INVENTION

The present invention relates to a novel setting solution for use in dental glass ionomer cements.

More particularly, the invention pertains to an aqueous setting solution for dental glass ionomer cements which consists of 45 to 60% of polyacrylic acid or acrylic acid copolymer and 7 to 25% of one or more of polybasic carboxylic acids based on the total weight.

Zinc phosphate cements are virtually the only dental adhesives which have been used world-wide for the past century. It has been pointed out, however, that zinc phosphate cement applied to a vital tooth often causes tooth pulp damage due to the irritating affect of the phosphoric acid which is an essential component of the solution. Zinc oxide-euginol cement irritates only slightly the pulp, but this type of cement has not found use in a permanent adhesive cement due to its poor strength and low water resistance.

On the other hand, zinc oxide - polycarboxylate cements using a setting solution composed primarily of an aqueous solution of polyacrylic acid in place of the phosphoric acid were developed by D. C. Smith et al of England in 1965, and are now spreading gradually. Many investigators report that the zinc oxide — polycarboxylate cements are characterized by causing almost no tooth pulp damage and possessing favorable adhesive properties. However, the adhesive strength of these cements is only one half of that of the zinc phosphate cement. Further work has developed the so-called "glass ionomer cement" in which a dental silicate cement is used in lieu of the primary component zinc oxide approximately 90,% and magnesium oxide approximately 10% of the conventional zinc oxide-polycarboxylate cement to obtain a new cement with a higher strength. This work has not succeeded in producing cements of sufficient strength and workability.

The present inventors have conducted various reaction, and found that a setting solution prepared by the combination of an aqueous solution of polyacrylic acid or acrylic acid copolymer and powders of silicate cement cannot be put into practical use. Upon completion of the mixing, this type of solution does not only prematurely form a rubbery mass to render further mixing difficult, but also produces a fluid mixture so that it is impossible to cement accurately a prosthesis to a tooth structure. In addition, a considerably long time interval is required for the completion of the setting rection, and the set product has an inferior strength.

In order to eliminate the above-mentioned drawbacks, the present inventors have discovered a glass ionomer cement of higher strength and translucent, clean appearance closed to natural teeth by using combinations of a 45 to 60 % aqueous solution of polyacrylic acid or acrylic acid copolymer with 7 to 25 % of one or more of polybasic carboxylic acids based on the total weight to powders for the glass ionomer cement.

This cement can be also used as a filling material for anterior teeth because of its excellent aesthetic appearance. As explained in the following examples, the cement is mixed to the filling consistency by varying the powder/liquid ratio; has physical properties superior to those of the conventional silicate cement, and does not undergo surface disintegration wherein it comes into contact with water during the setting reaction.

By using the setting solution for dental glass ionomer cements according to the present invention, the workability, strength and water resistance are improved and moreover the setting time is reduced. As powders for the glass ionomer cement, it is possible to use powders containing 37 to 45 % silicic anhydride, 25 to 45% aluminum oxide, 5 to 13% calcium oxide, 10 to 15% sodium fluoride and 3 to 7 % calcium phosphate.

The polybasic carboxylic acids used in the present invention include organic acids containing at least two carboxyl groups in the molecule, for example, citric acid, maleic acid, malic acid, tartaric acid, itaconic acid, aconitic acid, tricarballic acid or the like.

Since some of the polybasic carboxylic acids employed in the present inventions do not have a double bond, the copolymerization with the polyacrylic acid or acrylic acid copolymer the main component of the setting solution does not always occur. However, since all polybasic carboxylic acids more or less exhibit a reactivity with respect to the powders of the silicate cement, they are instrumental in improving the workability, strength and water resistance of the cement and in shortening the setting time thereof.

The amount of polybasic carboxylic acids used in the present invention may fall within the range of 7 to 25 %, preferably 10 to 15 %.

The acrylic acid copolymers employed in the present invention include those of acrylic acid and one or more of unsaturated aliphatic carboxylic acids such as 2 — chloroacrylic acid, 2 — bromoacrylic acid, maleic acid, fumaric acid, itaconic acid, methacrylic acid, mesaconic acid or the like or unsaturated compounds copolymerizable with acrylic acid, for example, acrylonitrile, methyl acrylate, methyl methacrylate, vinyl acetate, vinyl propionate, methyl itaconate, styrene, 2 — hydroxylethyl methacrylate etc.

The percentages of acrylic acid contained in a copolymer of acrylic acid used in the present invention may be more than 60 % by weight.

Polyacrylic acid or acrylic acid copolymer employed in the present invention has an average molecular weight of less than 30,000, preferably, 20,000 to 5,000. The desired molecular weight can be attained by using selectively a polymerization regulator with a proper chain transfer constant, for example, isopropyl alcohol, dodecyl mercaptan, thioglycolic acid or the like.

The average molecular weight referrred to herein is calculated on the basis of viscometry by the following method of calculation; the intrinsic viscosity $[\eta]$ is measured at 25° C in a 2N aqueous solution of sodium hydroxide and, then, the average molecular weight M is computed from the following emperical formula:

$$[\eta] = 1.21 \times 10^{-3} \times M^{0.54} \,(100 \text{ ml/g. } 25°C)$$

(Note: this formula is cited from Journal of the Chemical Society of Japan Sakamoto 83 386 (1962)

The setting solution for dental glass ionomer cements the present invention and is prepared by adding a predetermined amount of the polybasic carboxylic acids to an aqueous solution containing a predetermined percentage of polyacrylic acid or acrylic acid copolymer and allowing the resultant solution to stand.

The present invention will be now explained in detail by way of Examples 1 to 11 and Comparative Examples 1 to 5.

The setting solutions for dental glass ionomer cements, the compositions of which are shown in Table 1, were prepared by adding a given quantity of crystals of polybasic carboxylic acids to an aqueous solution containing the given percentage of polyacrylic acid or acrylic acid copolymer, shaking well the resultant solution, and leaving the solution enclosed in a container equipped with a stopper to stand at room temperature for 3 to 5 days until the solution turned into a colorless, transparent one.

On the other hand, the Comparative setting solutions composed of the components shown in Table 1 were prepared in the same manner as mentioned above.

In Table 1 all percentages are by weight.

TABLE 1

| Example | Composition of Setting Solut | |
|---|---|---|
| 1 | Polyacrylic acid (5000) | 51 % |
| | Pure water | 42 % |
| | Malic acid | 5 % |
| | Citric acid | 2 % |
| 2 | Polyacrylic acid (5000) | 50 % |
| | Pure water | 40 % |
| | Citric acid | 10 % |
| 3 | Polyacrylic acid (10000) | 50 % |
| | Pure water | 37 % |
| | Malic acid | 5 % |
| | Tartaric acid | 8 % |
| 4 | 90% acrylic acid/ 10% maleic acid copolymer (15000) | 50 % |
| | Pure water | 42 % |
| | Aconitic acid | 8 % |
| 5 | 85% acrylic acid / 15% fumaric acid copolymer (7000) | 50 % |
| | Pure water | 40 % |
| | Malic acid | 7 % |
| | Tricarballic acid | 3 % |
| 6 | 95% acrylic acid / 5% itaconic acid copolymer (12000) | 50 % |
| | Pure water | 39 % |
| | Tartaric acid | 8 % |
| | Aconitic acid | 3 % |
| 7 | Polyacrylic acid (6000) | 47 % |
| | Pure water | 45 % |
| | Tartaric acid | 8 % |
| 8 | 90% acrylic acid / 10% maleic acid copolymer (15000) | 52 % |
| | Pure water | 38 % |
| | Itaconic acid | 10 % |
| Comparative Example 1 | Polyacrylic acid | 50 % |
| | Pure water | 50 % |
| Comparative Example 2 | 90% acrylic acid / 10% maleic acid copolymer (15000) | 51 % |
| | Pure water | 49 % |
| Comparative Example 3 | 90% acrylic acid / 10% fumaric acid copolymer (8000) | 50 % |
| | Pure water | 47 % |
| | Tartaric acid | 3 % |

The bracket figure in Table 1 designates an average molecular weight of polyacrylic acid or acrylic acid copolymer, the molecular weight being computed according to the aforementioned method of calculation.

1.0 g of the thus obtained setting solution was mixed and kneaded for about 30 seconds with 1.4 g of the dental cement powders (made by G-C Dental Industrial Corp., Trade Name New Lusilex). The setting time, compressive strength and film thickness of the resultant product were measured according to the method set out in JIS T6602. (Said powders are prepared by sintering at high temperatures a material consisting of 40 % of silica sand, 26 % of alumina, 12 % of sodium fluoride, 15 % of lime carbonate and 7 % of lime phosphate).

The results are shown in Table 2 wherein the Comparative Example 4, i.e., the test results of the polycarboxylate cement made by E company and the specification of JIS T6602 relating to the zinc phosphate cement are also tabulated.

TABLE 2

| Example | Powder/liquid ration P/L (by weight) | Setting time (min.) | Compressive Strength after 24 hours (Kg/cm²) | Film thickness (micron) |
|---|---|---|---|---|
| 1 | 1.4/1.0 | 6.0 | 1420 | 30 |
| 2 | 1.4/1.0 | 5.5 | 1380 | 25 |
| 3 | 1.4/1.0 | 6.0 | 1330 | 28 |
| 4 | 1.4/1.0 | 6.5 | 1450 | 25 |
| 5 | 1.4/1.0 | 6.0 | 1510 | 30 |
| 6 | 1.4/1.0 | 6.5 | 1470 | 24 |
| 7 | 1.4/1.0 | 6.0 | 1530 | 25 |
| 8 | 1.4/1.0 | 6.0 | 1550 | 29 |
| Comparative Example 1 | 1.4/1.0 | 8.5 | 930 | 30 |
| Comparative Example 2 | 1.4/1.0 | 12.0 | 850 | 35 |
| Comparative Example 3 | 1.4/1.0 | 15.0 | 1090 | 25 |
| Comparative Example 4 | *1.5/1.0 | 6.5 | 540 | 25 |
| JIS | | 4~8 | more than 700 | less than 40 |

It is evident from the test results that the setting time according to this invention falls in the range of 5 to 6 minutes, this is considered most acceptable from a clinical viewpoint, and the compressive strength is about three times that of the conventional polycarboxylate cement. In addition, because of its excellent fluidity the mixed cement, when used to set a prosthetics to teeth, provides an extremely thin film in the order of 30μ so that it is possible to firmly cement inlays, crowns and bridges in place. It is further possible to reduce tooth pulp damage due to the phosphoric acid.

The setting time and compressive strength of the materials obtained by mixing for about 30 seconds 1.0 g of the setting solution of Examples 1 to 3 with 2.2 g of the aforementioned dental cement powders were measured according to the method set out in JIS T6603. The results are shown in Table 3 wherein the Comparative Example, i.e., the test results of the silicate cement made by W company and the specification of JIS T6603 concerning the silicate cement are also tabulated.

TABLE 3

| Example | Powder/liquid ration P/L (by weight) | Setting time (min.) | Compressive strength after 24 hours (Kg/cm²) |
|---|---|---|---|
| 9 | 2.2/1.0 | 4.0 | 2120 |
| 10 | 2.2/1.0 | 3.5 | 2210 |
| 11 | 2.2/1.0 | 4.5 | 2050 |
| Comparative Example 5 | 2.2/1.0 | 3.5 | 1890 |
| JIS | | 3~8 | more than 1500 |

The respective setting solutions used in Examples 9 to 11 have the same composition as those employed in Example 1 to 3.

As evident from these results, a glass ionomer cement using the setting solution of this invention affords a novel dental adhesive cement which eliminates deficiency inherent in the conventional polycarboxylate cement without affecting adversely the characteristic features thereof. In addition, this novel cement also affords a filling cement for anterior teeth which is free from the deficiencies of the conventional silicate cement by varying selectively a powder/liquid ratio.

What is claimed is:

1. An aqueous setting solution for dental ionomer cements comprising:
(a) 45 to 60% of a polymer having a molecular weight of less than 30,000 and selected from the group consisting of polyacrylic acid and a copolymer of acrylic acid and at least one monomer selected from the group consisting of 2-chloroacrylic acid, 2-bromoacrylic acid, maleic acid, fumaric acid, itaconic acid, methacrylic acid, mesaconic acid, acrylonitrile, methyl acrylate, methyl methacrylate, vinyl acetate, vinyl propionate, methyl itaconate, styrene and 2-hydroxylethyl methacrylate; and
(B) 7-25% of polybasic carboxylic acid selected from the group consisting of citric acid, maleic acid, malic acid, tartaric acid, itaconic acid, aconitic acid and tricarballic acid.

2. The aqueous setting solution of claim 1, wherein said polymer has a molecular weight of from 5,000 to 20,000.

3. The aqueous setting solution of claim 1, wherein from 10 to 15% of said polybasic carboxylic acid is present.

* * * * *

Notice of Adverse Decision in Interference

In Interference No. 100,540, involving Patent No. 4,089,830, C. Tezuka and Y. Karasawa, SETTING SOLUTION FOR DENTAL GLASS IONOMER CEMENTS, final judgment adverse to the patentees was rendered July 3, 1984, as to claims 1, 2, and 3.

[*Official Gazette April 30, 1985.*]